(12) United States Patent
Zhang et al.

(10) Patent No.: US 6,346,634 B1
(45) Date of Patent: Feb. 12, 2002

(54) CHEMICAL COMPOUND CONTAINING A SUPEROXIDE SCAVENGER AND AN ORGANIC NITRATE OR NITRITE MOIETY

(75) Inventors: Zhi Zhang, London; Declan P. Naughton, Brighton, both of (GB); Yoshihiko Sumi; Atsushi Imaizumi, both of Tokyo (JP)

(73) Assignee: Teijin Limited, Osaka (JP)

( * ) Notice: Subject to any disclaimer, the term of this patent is extended or adjusted under 35 U.S.C. 154(b) by 0 days.

(21) Appl. No.: 09/561,910

(22) Filed: May 1, 2000

(30) Foreign Application Priority Data

Apr. 30, 1999 (GB) ............................................. 9910104

(51) Int. Cl.⁷ .......................... C07C 50/02; C07C 50/12
(52) U.S. Cl. ........................................ 552/310; 552/296
(58) Field of Search .................................. 552/310, 296

(56) References Cited

FOREIGN PATENT DOCUMENTS

WO          99/37616         7/1999       ......... C07D/211/46

OTHER PUBLICATIONS

Cameron et al, Organic nitrates, thionitrates, peroxynitrites, and nitric oxide, Can. J. Chem., vol. 73, No. 10, pp 1627–1638, 1995.*

Manecke et al, Vinyl–1,4–naphthoquinones, Chem. Ber., 1967m vol. 100, No. 3 pp. 836–844, 1967.*

* cited by examiner

*Primary Examiner*—Alton Pryor
(74) *Attorney, Agent, or Firm*—Sughrue, Mion, Zinn, Macpeak & Seas, PLLC

(57) ABSTRACT

Compounds for use in the treatment of heart disease include a superoxide scavenger and an organic nitrate or nitrite moiety. The compounds can be represented by the formula (A)n(B)m, in which A is a superoxide scavenger, B is an organic nitrate or organic nitrite moiety, and n and m are values between 1 and 8. These compounds do not suffer from the problem of patient tolerance that is associated with the use of conventional agents such as organic nitrates.

1 Claim, 1 Drawing Sheet

FIGURE
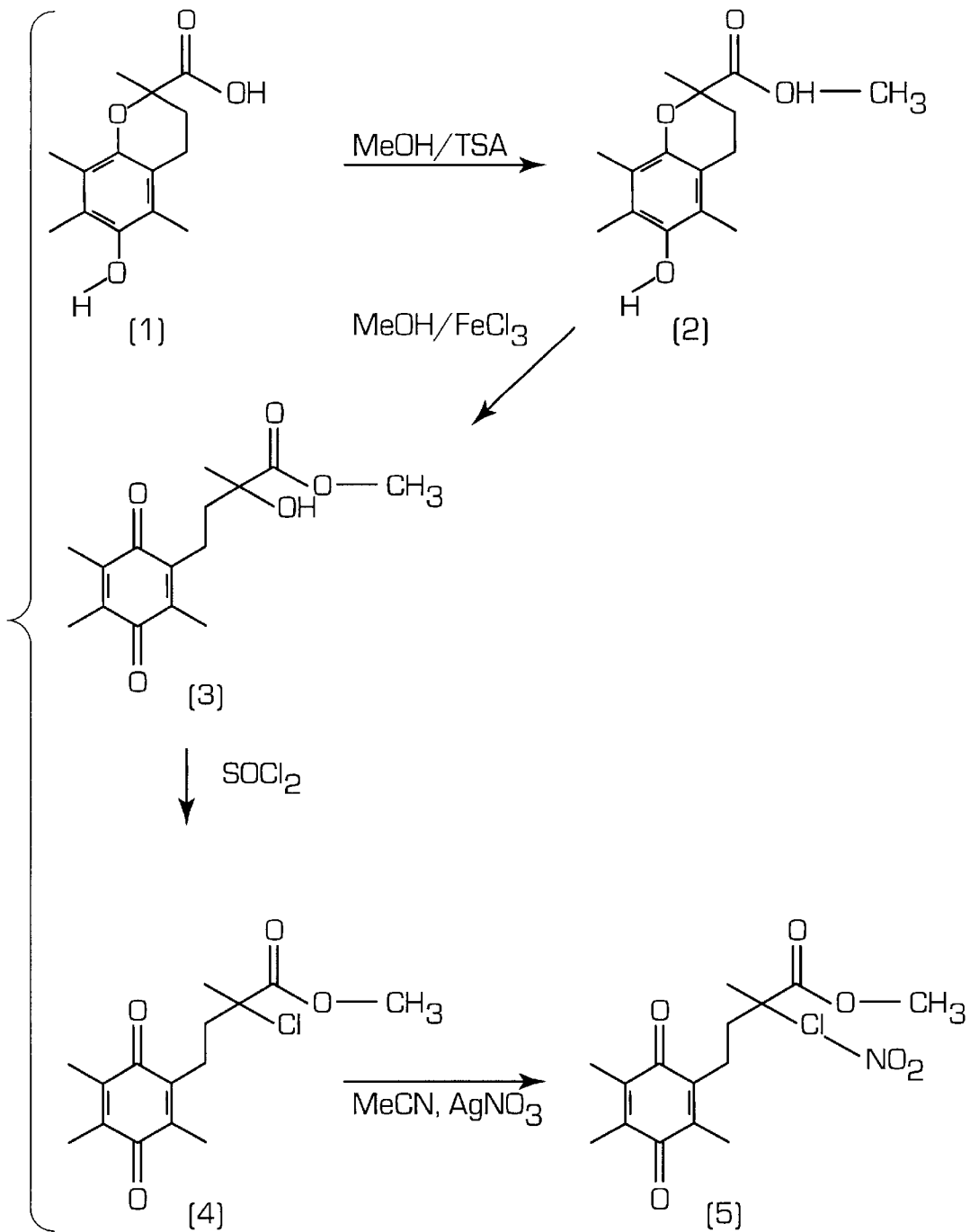

CHEMICAL COMPOUND CONTAINING A SUPEROXIDE SCAVENGER AND AN ORGANIC NITRATE OR NITRITE MOIETY

FIELD OF THE INVENTION

The present invention relates to compounds suitable for use in the treatment of heart disease. These compounds do not suffer from the problem of patient tolerance that is associated with the use of conventional agents such as organic nitrates.

BACKGROUND OF THE INVENTION

Organic nitrates and nitrites have been widely prescribed for the prophylactic treatment of angina for over 100 years. More recently, these drugs have been extended to manage coronary artery disease, acute myocardial infarction and congestive heart failure (Parker & Parker, (1998) *N. Engl. J. Med.* 338; 520–531). Examples of such drugs include glyceryl trinitrate (GTN), 1,2-glyceryl dinitrate, 1,3-glyceryl dinitrate, isosorbide dinitrate, isosorbide-2-mononitrate and isosorbide-5-mononitrate.

The primary action of organic nitrates is vasodilation, which is attributable primarily to nitrate-induced relaxation of vascular smooth muscle in veins, arteries, and arterioles. Organic nitrates are converted in the body to endothelium-derived relaxing factors (EDRFs), which act to dilate vascular smooth muscle and to inhibit platelet aggregation by activating guanylyl cyclase and increasing intracellular cyclic-3',5'-guanosine monophosphate (cGMP). This represents the cellular basis for the vasodilatory action of organic nitrates.

Organic nitrate administration has been used as a means of providing an exogenous source of EDRF that may help replenish or restore endogenous EDRF levels that are usually impaired in patients with coronary artery diseases such as atherosclerosis.

Discovered to be an EDRF, nitric oxide (NO) is an important endogenous modulator of vascular tone (Ignarro et al., (1987) *Proc. Natl. Acad Sci U.S.A.* 84:9265–9269; Palmer et al, (1987) *Nature* 327:524–526). A great deal of interest has been shown in the in vivo metabolism of organic nitrates to produce NO. However, the cellular mode of action of organic nitrates, in particular, the details of nitrate to NO bio-transformation, still remain unclear. It has been suggested that bio-transformation of organic nitrates to NO is a thiol-dependent enzymatic denitration process catalyzed by glutathione-s-transferase and the cytochrome P450-NADPH cytochrome P450 reductase system (Bennette et al., (1994) *Trends Pharmacol. Sci.* 15; 245–249). However, it has since been discovered that glutathione-s-transferase catalyzes the reduction of organic nitrate to nitrite, and does not catalyze the reduction of nitrite to NO.

The major problem with nitrate therapy is the rapid development of tolerance and cross-tolerance during repeated dosing with these agents (Parker & Parker, 1998). Clinically, intermittent dosing regimens that allow for a drug-free interval represent the only practical and effective strategy for avoiding nitrate tolerance. Clearly, the need to interrupt drug administration regularly reduces the effectiveness of this form of therapy.

Nitrate tolerance is believed to be a complex multi-factorial phenomenon, and the underlying mechanism of organic nitrate tolerance is poorly understood. One possible route of nitrate tolerance is due to a relative depletion of sulfhydryl groups required for bio-conversion of organic nitrates to NO. More recently it has been suggested that enhanced vascular superoxide production from endothelium plays an important role in this phenomenon (Munzel et al., (1995) *J. Clin. Invest.* 95:187–194; Rajagopalan et al, (1996) *J. Clin. Invest.* 97:1916–1923).

There thus remains a great need for compounds that are effective in the body as vasodilators and which may be administered continuously for a sustained period of time without suffering a reduction in efficacy due to development of patient tolerance.

SUMMARY OF THE INVENTION

According to the present invention there is provided a compound comprising a scavenger of superoxide and an organic nitrate or nitrite moiety. Such compounds are effective vasodilators, yet do not exhibit the problems of patient tolerance to nitrates, from which conventional vasodilatory agents suffer.

BRIEF DESCRIPTION OF THE DRAWINGS

The Figure shows a reaction scheme for preparing a superoxide scavenger-organic nitrate ester.

DETAILED DESCRIPTION OF THE INVENTION

The advance that led to the development of the compounds of the invention is based on the inventors' observation of a novel molecular mechanism of the bio-conversion of organic nitrate to NO by xanthine oxidase (XO). The XO enzyme is a homodimer of 150 kDa subunits, and contains four oxidation and reduction centers, one molybdenum cofactor, one flavin adenine dinucleotide (FAD) and two [$Fe_2S_2$] clusters. XO catalyzes the oxidative hydroxylation of a range of aromatic heterocyclic compounds of which the most notable are hypoxanthine and xanihine. During the process of purine metabolism, XO catalyzes the two-step oxidation of hypoxanthine, through xanthine, to uric acid. The oxidation of hypoxanthine or xanthine is concomitantly accompanied by the reduction of oxygen to form superoxide and $H_2O_2$ (see Table 1, reaction scheme I).

TABLE 1

| Reactions catalyzed by XO | | |
|---|---|---|
| Xanthine oxidase activity | $XH + H_2O + O_2 \rightarrow X = O + H_2O_2 + O_2^{\cdot-}$ | I |
| NADH oxidase activity | $2NADH + 2O_2 \rightarrow NAD + O_2^{\cdot-} + H_2O_2$ | II |
| Nitrate reductase activity | $2NO_3^- \rightarrow NO_2^{\cdot} + O_2$ | III |
| Nitrite reductase activity | $2NADH + 2NO_2^{\cdot} \rightarrow 2NAD + H_2O_2 + 2NO^{\cdot}$ | IV |

Despite being a reducing agent that is itself capable of causing significant damage to biomolecules, such as by initiating lipid peroxidation, superoxide is considered to be the most important source of oxidative stress. It can be rapidly converted to the highly toxic hydroxyl radical via the Fenton reaction or the Haber-Weiss reaction. It can also react rapidly with NO to form deleterious diffusion-controlled peroxynitrate (Beckman et al., (1990) *Proc. Natl. Acad Sci. U.S.A.* 87;1620–1624). Both hydroxyl radicals and peroxynitrate have been shown to initiate lipid peroxidation, protein and enzyme inactivation and DNA fragmentation. On this basis, the classical pathway of superoxide production by XO (see Table 1, reaction scheme I) has been implicated as constituting a major role in a number of pathogenic conditions, such as atherosclerosis, hypercholesterolaemia, diabetes mellitus and rheumatoid arthritis.

In particular, the role of XO in the generation of excess superoxide during hypoxic reperfusion injury has received a great deal of attention (McCord J. M. (1985) *N. Engl. J. Med.* 312:159–163). During ischaemia, endogenous xanthine dehydrogenase is converted to XO. Concomitantly, hypoxanthine and xanthine are accumulated as a consequence of ATP breakdown. The reperfusion phase following ischaemia allows the XO to use accumulated hypoxanthine or xanthine together with oxygen to produce a burst of tissue-damaging superoxide and $H_2O_2$.

In addition to the above-described classical reaction of XO, early studies have shown that XO can use NADH as a reducing substrate, possibly binding at a site different from that at which xanthine binds. However, this NADH oxidase activity of XO is not generally recognized and has been little studied over the years.

Several recent studies have suggested that endothelium and vascular smooth muscle contain membrane-bound NADH oxidase enzymes that use NADH as a substrate to produce superoxide (Sanders et al., (1997) *Eur. J. Biochem.* 289:523–527). The inventors' previous research and that of others has demonstrated that human XO can use not only hypoxanthine or xanthine (Table 1, reaction scheme I) but also NADH (Table 1, reaction scheme II) as a substrate to generate superoxide (Zhang et al., (1998) *Free Rad. Res.* 28;151–164).

This NADH-oxidizing activity of XO is blocked by diphenyleneiodonium (DPI) but is not suppressible by the conventional xanthine-based inhibitors, such as allopurinol, oxypurinol, BOF-4272 and Amfiutizole. Therefore, apart from the xanthine-based free radical-generating pathway, the NADH oxidase activity of XO may operate as an additional pathway to produce free radicals. In other words, XO can contribute to tissue damage depending on which substrate is available in pathological situations.

The third and less well-known phenomenon by XO is that this enzyme is capable of catalyzing the reduction of nitrate to nitrite under anaerobic conditions (Table 1, reaction scheme III). Although the nitrate reductase activity of XO has long been known (Fridovich and Handler (1962) *J. Biol. Chem.*, 237:916–921), it has been little studied and is not generally recognized. This property of the enzyme is shared with the assimilatory nitrate reductase of bacteria, algae and fungi (Payne et al., (1997) *BioFactors* 9:1–6). Both enzymes are molybdoenzymes containing FAD redox centers and utilizing NAD(P)H as a reducing substrate to catalyze the reduction of nitrate to nitrites.

In a recent paper, the inventors investigated the possible mechanism of nitrite reductase activity of XO by directly detecting NO formation (Zhang et al., (1998) *Biochem. Biophys. Res. Commun.* 249;767–772). It was found that XO catalyzes the reduction of nitrite to NO with NADH as a source of electrons (Table 1, reaction scheme IV). This reductive reaction occurs regardless of environmental oxygen tension, i.e. XO can reduce nitrite in both the presence or absence of oxygen once an electron donor is available. By using two different site-directed XO inhibitors, allopurinol and DPI, it was found that the reduction of nitrite takes place at the molybdenum center of XO, while NADH is oxidized at the FAD center. This reaction pathway may play a very important role in redistribution of blood flow to ischaemic tissue by virtue of the vasodilatory effect of NO, since conventional NO synthesis by nitric oxide synthase (NOS) is impaired under ischaemic conditions.

More importantly, the nitrate and nitrite reductase activities of XO has allowed the inventors to develop a novel explanation for the bio-transformation of organic nitrates to NO in organic nitrate and nitrite therapy of angina pectoris. Indeed, it has been found that XO catalyzes not only the reduction of nitrite to NO, but also the reduction of organic nitrates such as glyceryl trinitrate to NO.

During the catalytic reduction of nitrite at the molybdenum center of XO, oxidation is concomitantly required at the FAD site using NADH as its electron donor. In the absence of oxygen, this reaction will only generate NO from the molybdenum center. However, in the presence of oxygen, XO exhibits not only nitrite reductase activity (Table 1, reaction scheme IV) but also NADH oxidase activity (Table 1, reaction scheme II). Thus, oxygen will act as an electron acceptor along with nitrite and produce superoxide. Although NO and superoxide may be generated at different redox sites, it is proposed that the simultaneous production of both radicals by the same XO enzyme will result in the formation of peroxynitrate and decrease the net production of NO formation by XO. Increased vascular superoxide production during continuous dosing inactivates NO by forming peroxynitrate, which consequently inhibits NO-mediated vasorelaxation produced by organic nitrates.

Peroxynitrate itself is a non-selective and extremely reactive ion. Its deleterious function inactivates or modifies not only large molecules such as metalloenzymes, but also small molecules, for example, thiols. The formation of peroxynitrate is thus proposed to lead to both the inactivation of XO and the depletion of thiols at one specific enzyme site. The inventors propose that this inactivation, together with the mopping-up effect of superoxide on NO explains the hitherto unsolved phenomenon of nitrate tolerance.

As a result of these observations on XO, novel compounds have been designed that are generators of organic nitrates. These compounds are hybrid molecules, comprising both a superoxide scavenger and a generator of NO. The new agents may be expected to diminish nitrate tolerance by at least two mechanisms: (1) the reduction of NO and superoxide interaction and (2) the reduction in superoxide-mediated thiol depletion, by scavenging superoxide produced by NADH oxidation.

In the present invention, the organic nitrate or nitrite moiety forms nitric oxide in the body of an animal. The organic nitrate or nitrite moiety should be converted metabolically to NO by endogenous enzymes in the animal body. By animal is meant any animal, although mammals, preferably humans, are considered to be the most appropriate patients for therapy of heart disease. In accordance with the conclusions discussed above, a principle mechanism by which the organic nitrate or nitrite moiety is proposed to be converted to NO is by action of XO in the body. However, any mechanism of metabolic conversion of organic nitrate or nitrite to NO is compatible with the method of action of the compounds of the invention, and any mechanism of metabolic conversion of organic nitrate or nitrite to NO is compatible with the conversion of the compounds of the invention to NO. In addition, the proximity of the hybrid anti-oxidant scavengers can avert reactive oxygen species-mediated NO consumption or further production of deleterious species.

The superoxide scavenger portion of the compounds of the invention may be any one of a large number of compounds that are known to be effective scavengers of superoxide. Examples include spin-traps such as DMPO, low molecular mass superoxide dismutase (SOD) analogs such as the Cu(salicylate)$_2$ complex, redox active transition metal complexes such as FeIII EDTA, zinc carnosine complexes, antioxidants such as desferrioxamine and substrates for direct redox reactions with superoxide such as cytochrome-c and vitamin E. Preferably, the superoxide scavenger is a spin trap that is capable of trapping superoxide. One or more thiol moieties may form part of the superoxide scavenger.

Linkage of the superoxide scavenger to the organic nitrate or nitrite moiety may be through any one of a number of known chemical bonds including ester, amide and ether bonds. Preferably, the linkage itself is resistant to enzymatic degradation. Linkage via a thiol ester is considered to be particularly preferable, since the use of this linkage will reduce the thiol load that is necessary for activation of the organic nitrate moiety in the body. The use of this linkage will thus further minimize tolerance of a patient to organic nitrate-derived NO.

According to a further aspect of the invention, there is provided compound according to formula I:

where A is a scavenger of superoxide and B is an organic nitrate or organic nitrite moiety. "m" and "n" may be any number, although it is envisaged that the values of m and/or n will not generally exceed about 8. Desirably, m and n are values between 1 and 8. Preferably, m and n are integers. Particularly preferably, the values of m and n are both 1.

Preferably, A and B are stably linked. By "stably linked" is meant that the chemical bond that joins the superoxide scavenger moiety and the organic nitrate or nitrite is stable to degradation under physiological conditions. This increases the therapeutic capacity of the compound, since it will not be inappropriately broken down by the metabolism of the body to form compounds that are not functional as either superoxide scavengers or generators of NO. A preferable linkage is a thiol linkage. Ideally, the linkage should also be stable at room temperature and pressure, to increase the shelf-life of the compound. Ideally, the linkage should also be stable or stabilizable at storage temperature.

In order that both the superoxide scavenger and NO-generating functions of the compound are fully exploited, the superoxide scavenger moiety should remain active in trapping superoxide after conversion of the organic nitrate or nitrite to NO.

A particularly preferred compound according to the invention is the nitrate ester (5), the structure of which is illustrated in the Figure. This compound is proposed to be particularly effective in minimizing superoxide interaction with NO upon the conversion of the organic nitrate moiety in the compound.

According to a further aspect of the invention, there is provided a composition containing one or more compounds as described above, in conjunction with a pharmaceutically-acceptable excipient. Suitable excipients will be well known to those of ordinary skill in the art and may, for example, comprise a phosphate-buffered saline, a liquid such as water, saline, glycerol or ethanol, optionally also containing mineral acid salts such as hydrochlorides, hydrobromides, phosphates, sulphates and the like; and the salts of organic acids such as acetates, propionates, malonates and benzoates. Auxiliary substances such as wetting or emulsifying agents and pH buffering substances may also be present. A thorough discussion of pharmaceutically acceptable excipients is available in Remington's Pharmaceutical Sciences (Mack Pub. Co., N.J. 1991).

According to a still further aspect of the invention there is provided a compound or a composition as described above, for use as a pharmaceutical. Such compounds or compositions are suitable for the preventative or curative therapy of a wide variety of pathological conditions associated with endothelial dysfunction, in particular coronary artery diseases such as atherosclerosis and hypertension, and rheumatoid arthritis, diabetes and neurodegenerative diseases. The invention also embraces methods of therapy of heart disease comprising administering to a patient an effective amount of a compound or composition as described above.

Various aspects and embodiments of the present invention will now be described in more detail by way of example, with particular reference to an antioxidant nitrate ester. It will be appreciated that modification of detail may be made without departing from the scope of the invention. All documents mentioned in the text are incorporated herein by reference.

BRIEF DESCRIPTION OF THE DRAWINGS

The FIG. 1 is a reaction scheme illustrating the preparation of superoxide scavenger-organic nitrate ester (5), and is discussed in greater detail below.

EXAMPLES

Example 1

Synthesis of Antioxidant Nitrate Ester

Step 1:

A solution of 2 g (8 mmol) of optically pure (R)-(+)-3,4-dihydro-6-hydroxy-2,5,7,8-tetramethyl2 H-1-benzopyran-2-carboxylic acid (1) and 0.1 g of p-toluenesulphonic acid monohydrate in 40 ml methanol were stirred and re-fluxed for 4 hours. After cooling, the solution was diluted with water, extracted three times into ether that was subsequently washed with brine and aqueous sodium bicarbonate solution. The ether solution was washed, dried with MgSO$_4$ and evaporated to give (R)-(+)-methyl 3,4-dihydro-6-hydroxy-2,5,7,8-tetramethyl-2 H- 1-benzopyran-2 carboxylate (2).

Step 2:

To a stirred solution of 1.5 g (5.68 mmol) of (2) in 22 ml ether, was added a solution of 4.5 g (16.6 mmol) of ferric chloridehexahydrate in 17 ml of water and 17 ml of methanol. The addition was carried out drop-wise over 30 minutes. After 1 hour the ether layer was separated, and the aqueous phase was further extracted with ether. The combined ether layers were chromatographed on silica gel by flash chromatography using toluene-ethyl acetate as the eluant to provide 1.39 g of the oxidized quinone (R)-(+)-methyl 2-hydroxy-2-methyl-4-(3,4,5-trimethyl- 3,6-dioxo- 1,4-cyclohexadien-1-yl)butanoate(3).

Step 3:

A solution of 0.5 g of the tertiary alcohol (3) in dry dichloromethane (20 ml) was charged 5 with SOCl$_2$ (5 ml) and stirred at room temperature for 30 minutes. The resulting solution was evaporated in a vacuum and re-dissolved in ethyl acetate. This procedure was repeated twice to remove residual SOC$_{12}$. The chlorinated product (R)-(+)-methyl 2-chloro-2-methyl-4-(3,4,5 trimethyl-3,6-dioxo- 1,4-cyclohexadien- 1-yl)butanoate (4) was used without further purification.

Step 4:

To a stirring solution 0.1 g of (4) in dry acetonitrile at room temperature was added one equivalent of silver nitrate (AgNO$_3$). A precipitate of silver chloride formed. The reaction mixture was stirred for a further 30 minutes and was then filtered and evaporated. The nitrate ester (5) was purified on silica gel chromatography using $CHCl_2$ and ethyl acetate as the eluant.

Example 2

Exemplification of Protective Effect of Antioxidant

Buffered solutions containing an organic nitrate as follows [all containing vitamin C between 1 and S equivalents]: (i) propyl nitrate, (ii) propyl nitrate plus one equivalent of compound (3) and (iii) compound (S) in the range of 1 to 10 μmol were prepared. These solutions were incubated in sealed glass vessels with appropriate concentrations of XO and NADH under both hypoxic and normoxic conditions. After 24 hours levels of NO were measured by aspirating the glass vessels and monitoring NO concentration directly. The results demonstrated the ability of superoxide scavengers to minimize superoxide interaction with NO upon activation of organic nitrates.

While the invention has been described in detail with reference to specific embodiments thereof, it will be apparent to one of ordinary skill in the art that various changes and modifications can be made therein without departing from the spirit and scope thereof.

What is claimed is:
1. A compound having the formula

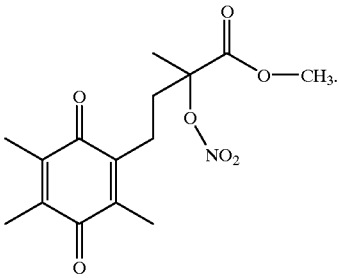

* * * * *